United States Patent [19]

Nagano et al.

[11] Patent Number: 4,701,399
[45] Date of Patent: Oct. 20, 1987

[54] PHOTOSENSITIVE COMPOSITION WITH 2-HALOMETHYL-5-SUBSTITUTED-1,3,4-OXADIAZOLE

[75] Inventors: Teruo Nagano, Kanagawa; Tadao Toyama; Akira Nagashima, both of Shizuoka, all of Japan

[73] Assignee: Fuji Photo Film Co., Ltd., Kanagawa, Japan

[21] Appl. No.: 705,265

[22] Filed: Feb. 25, 1985

[30] Foreign Application Priority Data

Feb. 24, 1984 [JP] Japan .................... 59-34080

[51] Int. Cl.$^4$ .................. G03C 1/60; G03C 1/70; G03C 1/71; G03C 1/727
[52] U.S. Cl. .................. 430/179; 430/175; 430/191; 430/196; 430/281; 430/283; 430/284; 430/285; 430/286; 430/287; 430/920; 430/925; 548/143
[58] Field of Search ........... 430/920, 925, 285, 175, 430/179, 191, 196, 281, 283, 284, 287, 286; 548/143

[56] References Cited

U.S. PATENT DOCUMENTS

| | | | |
|---|---|---|---|
| 3,558,316 | 1/1971 | Keberle et al. | 430/933 |
| 4,104,468 | 8/1978 | Valenti | 548/143 |
| 4,212,970 | 7/1980 | Iwasaki | 430/925 |
| 4,232,106 | 11/1980 | Iwasaki et al. | 430/920 |
| 4,279,982 | 7/1981 | Iwasaki et al. | 430/920 |
| 4,282,309 | 8/1981 | Laridon et al. | 430/920 |

*Primary Examiner*—Charles L. Bowers, Jr.
*Attorney, Agent, or Firm*—Sughrue, Mion, Zinn, Macpeak & Seas

[57] ABSTRACT

A photosensitive composition containing a 2-halomethyl-5-substituted-1,3,4-oxadiazole compound represented by the following general formula (I):

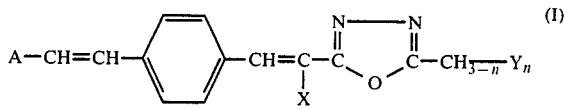

wherein A represents a substituted or unsubstituted aromatic residue; X represents a hydrogen atom, a cyano group, an alkyl group or an aryl group; Y represents a chlorine atom or a bromine atom; and n represents an integer of 1 to 3.

The free radical generating agent represented by the general formula (I) has a photosensitive wavelength range from near ultraviolet range to visible range, high photo-decomposition sensitivity and good compatibility with other components present in the photosensitive composition.

The photosensitive composition is suitable for use in light-sensitive printing plates or photo-resists.

9 Claims, No Drawings

PHOTOSENSITIVE COMPOSITION WITH 2-HALOMETHYL-5-SUBSTITUTED-1,3,4-OXADIAZOLE

FIELD OF THE INVENTION

The present invention relates to a photosensitive composition containing a novel compound which generates a free radical upon exposure to light. In greater detail, it relates to a photosensitive composition containing a novel 2-halomethyl-5-substituted-1,3,4-oxadiazole compound.

BACKGROUND OF THE INVENTION

Compounds which decompose upon exposure to light to generate free radicals (free radical generating agents) are well known in the field of graphic arts. They have been widely used as photopolymerization initiators in photopolymerizable compositions, as photoactivators in free radical photographic compositions and as photo initiators for reactions catalyzed by acids formed by light. Using such free radical generating agents, various photosensitive materials useful for printing, duplicating, copying or other image formation are produced.

Organic halide compounds decompose upon exposure to light to generate halogen free radicals such as a chlorine free radical or a bromine free radical. These halogen free radicals are good hydrogen abstracting agents and form acids when a hydrogen donor is present. Application of such halide compounds to photopolymerization processes and free radical photographic processes have been described in *Light-Sensitive Systems* written by J. Kosar, pages 180 to 181 and 361 to 370, J. Wiley & Sons (New York, 1965).

As such compounds which generate halogen free radicals as a function of light, carbon tetrabromide, iodoform and tribromoacetophenone are typical examples which have been widely used heretofore. However, these free radical generating agents suffer from the drawback that they decompose only upon exposure to light in a limited wavelength range. Namely, they are sensitive to light in an ultraviolet range which is shorter than the main wavelength of the light sources generally used. These compounds have a poor free radical generating capability, because they do not have the ability of effectively utilize the light of near ultraviolet range to visible range.

For the purpose of overcoming this drawback, it has been proposed to expand the photosensitive wavelength range by adding certain kinds of sensitizers. There are, for example, sensitizers such as merocyanine dyes, styryl bases and cyanine bases, as disclosed in U.S. Pat. Nos. 3,106,466 and 3,121,633. Although the addition of these sensitizers expands the sensitive wavelength range of carbon tetrabromide or iodoform to the visible range, the result is still not satisfactory since it is difficult to select a sensitizer which has good compatibility with the free radical generating agents or other components in the photosensitive composition and has high sensitivity, although selection of the sensitizer having such compatibility is necessary.

In order to overcome this drawback, halogen free radical generating agents which have the photosensitive wavelength range in the near ultraviolet range to the visible range have been proposed. For example, halomethyl-s-triazine compounds are described in U.S. Pat. Nos. 3,954,475, 3,987,037 and 4,189,323. Although these compounds have a photosensitive wavelength range in the near ultraviolet range to visible range, their photodecomposition sensitivities are relatively low since light exposed is not utilized effectively.

SUMMARY OF THE INVENTION

Accordingly, an object of the present invention is to provide a photosensitive composition which contains a free radical generating agent having a photosensitive wavelength range in the near ultraviolet range to the visible range and having high photo-decomposition sensitivity.

Another object of the present invention is to provide a free radical generating agent having good compatibility with other components present in the photosensitive composition.

These and other objects of the present invention will become more apparent from the following description of the invention.

As the result of various investigations in this field, the present inventors have discovered a novel 2-halomethyl-5-substituted-1,3,4-oxadiazole compound represented by the following general formula (I) which is useful as a free radical generating agent for attaining the above described objects:

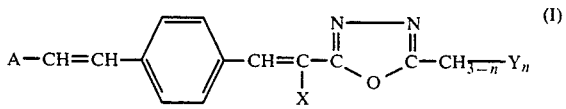

wherein A represents a substituted or unsubstituted aromatic residue, X represents a hydrogen atom, a cyano group, an alkyl group or an aryl group; Y represents a chlorine atom or a bromine atom; and n represents an integer of 1 to 3.

DETAILED DESCRIPTION OF THE INVENTION

In the general formula (I), the aromatic residue represented by A includes an aryl group and a hetero aromatic residue, and is preferably a monocyclic or bicyclic group. Examples of the aromatic residue include a phenyl group, a 1-naphthyl group, a 2-naphthyl group, a 2-furyl group, a 2-thienyl group, a 2-oxazolyl group, a 2-thiazolyl group, a 2-imidazolyl group, a 2-pyridyl group, a 2-benzofuryl group, a 2-benzothienyl group, a 2-benzoxazolyl group, a 2-benzothiazolyl group, a 2-benzimidazolyl group, a benzotriazolyl group, a 2-indolyl group, a 2-quinolyl group, etc.

The substituted aromatic residue represented by A includes the above-described aromatic residue which is substituted with an alkyl group having from 1 to 2 carbon atoms (for example, a methyl group, an ethyl group, etc.), an alkoxy group having from 1 to 2 carbon atoms (for example, a methoxy group, an ethoxy group, etc.), a halogen atom (for example, a chlorine atom, etc.), a nitro group, a phenyl group, a carboxy group, a cyano group, etc. Specific examples of the substituted aromatic residue include a 4-chlorophenyl group, a 2-chlorophenyl group, a 4-bromophenyl group, a 4-nitrophenyl group, a 3-nitrophenyl group, a 4-phenylphenyl group, a 4-methylphenyl group, a 2-methylphenyl group, a 4-ethylphenyl group, a 4-methoxyphenyl group, a 2-methoxyphenyl group, a 4-ethoxyphenyl group, a 2-carboxyphenyl group, a 4-cyanophenyl group, a 3,4-methylenedioxyphenyl group, a 4-phenoxyphenyl group, a 4-acetoxyphenyl group, a 4-methyl-1-naphthyl group, a 4-chloro-1-naphthyl group, a 5-nitro-1-naphthyl group, a 6-chloro-2-naphthyl group, a 4-bromo-2-naphthyl group, a 5-nitro-2-naphthyl group, a 6-methyl-2-benzofuryl group, a 6-methyl-2-benzoxazolyl group, a 6-methyl-2-benzothiazolyl group, a 6-chloro-2-benzothiazolyl group, etc.

The alkyl group represented by X is preferably an alkyl group having from 1 to 3 carbon atoms and includes, for example, a methyl group, an ethyl group, a n-propyl group, etc.

The aryl group represented by X is a monocyclic or bicyclic aryl group and includes, for example, a phenyl group, a 1-naphthyl group, a 2-naphthyl group, etc.

The 2-halomethyl-5-substituted-1,3,4-oxadiazole compounds represented by the above-described general formula (I) which can be used in the present invention can be synthesized in the following steps of procedure.

That is, a compound represented by the following general formula (II):

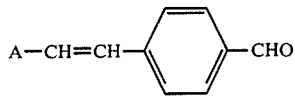

(II)

(wherein A has the same meaning as defined in the general formula (I)) is synthesized according to the method as described in *Journal fur Praktische Chemie*, Vol. 4, pages 124 to 129 (1956) written by G. Drefahl et al., the method as described in *Journal of Medical Chemistry*, Vol. 14, pages 315 to 322 (1971) written by B. R. Baker et al., or the method as described in *Journal of the Chemical Society, Perkin Transactions I*, pages 1 to 6 (1979) written by J. Castells et al., etc.

Then, using the compound represented by the general formula (II) as a starting material, an acrylic acid derivative represented by the following general formula (III):

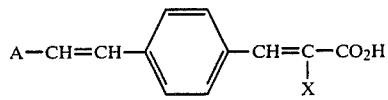

(III)

(wherein A and X each has the same meaning as defined in the general formula (I)) can be synthesized in a conventional manner.

The acrylic acid derivative represented by the general formula (III) can be converted to an acrylic acid hydrazide derivative represented by the following general formula (IV):

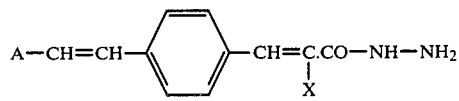

(IV)

(wherein A and X each has the same meaning as defined in the general formula (I)) in accordance with the method as described in *Acta Chimica Scandinavica*, Vol. 9, pages 1498 (1955) written by W. O. Godtfredsen et al or the method as described in *Bulletin of the Chemical Society of Japan*, Vol. 41, page 2521 (1968) written by H. Kondo et al., etc.

The acrylic acid hydrazide derivative represented by the general formula (IV) is subjected to reaction in accordance with the method described in U.S. Pat. No. 4,232,106 or the method described in West German Patent Application (OLS) No. 2,851,471 to obtain a 2-halomethyl-5-substituted-1,3,4-oxadiazole compound represented by the general formula (I) described above.

Compounds having the structure shown below are particularly advantageous as the free radical generating agent used in the present invention.

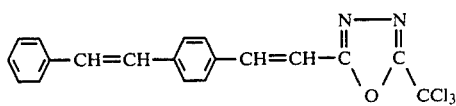

No. 1

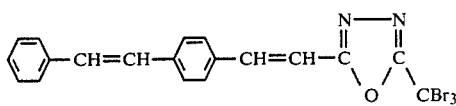

No. 2

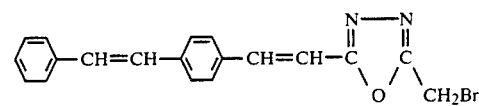

No. 3

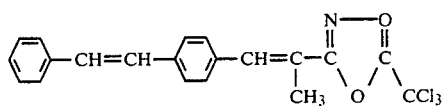

No. 4

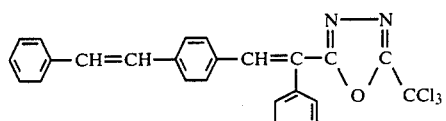

No. 5

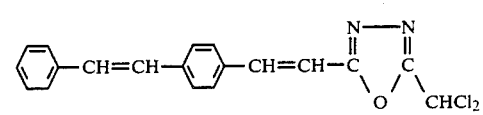

No. 6

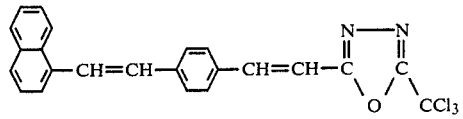

No. 7

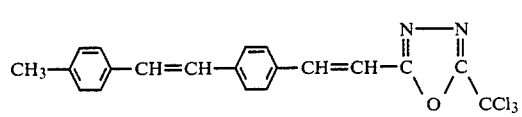

No. 8

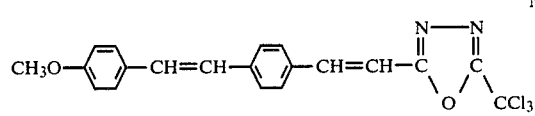

No. 9

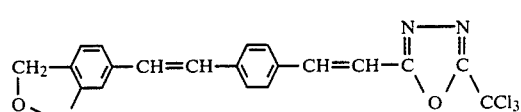

No. 10

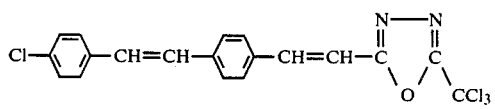
No. 11

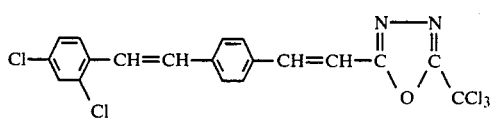
No. 12

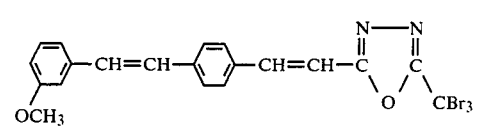
No. 13

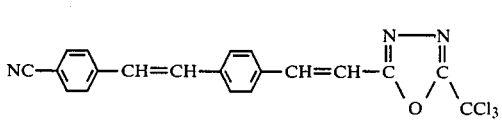
No. 14

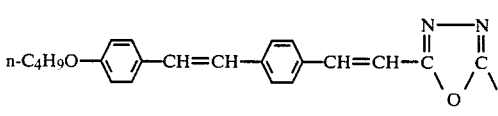
No. 15

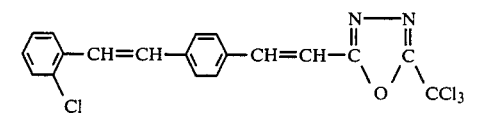
No. 16

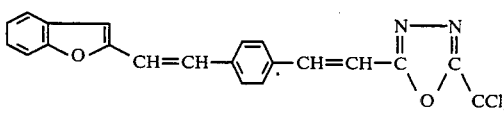
No. 17

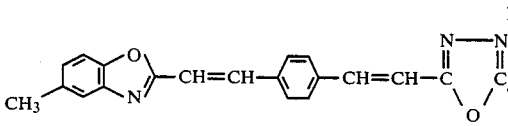
No. 18

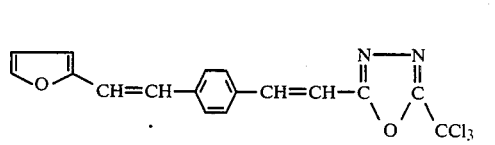
No. 19

The free radical generating agents according to the present invention are useful as photopolymerization initiators for photopolymerizable compositions. Photopolymerizable compositions are composed of a polymerizable compound having an ethylenically unsaturated bond and a photopolymerization initiator, and, if necessary, a binder, and further, if necessary, a sensitizer. These photopolymerizable compositions are particularly useful for a light-sensitive layer of light-sensitive printing plates, photoresists, etc.

The polymerizable compound having an ethylenically unsaturated bond used in the photopolymerizable composition of the present invention is a compound having at least one ethylenically unsaturated bond in the chemical structure thereof and has the chemical form of a monomer, a prepolymer (i.e., a dimer, a trimer and other oligomers), a mixture of monomer or prepolymer or a copolymer of monomer and prepolymer. Examples of the compound include unsaturated carboxylic acids, salts of unsaturated carboxylic acids, esters of unsaturated carboxylic acids and aliphatic polyhydric alcohol compounds, amides of unsaturated carboxylic acids and aliphatic polyvalent amine compounds, etc.

Specific examples of unsaturated carboxylic acids used as the foregoing compounds in the present invention include acrylic acid, methacrylic acid, itaconic acid, crotonic acid, isocrotonic acid, maleic acid, etc.

Examples of salts of unsaturated carboxylic acids include sodium salts and potassium salts of the aforesaid unsaturated carboxylic acids.

Specific examples of the esters of unsaturated carboxylic acids and aliphatic polyhydric alcohol compounds include acrylic acid esters such as ethylene glycol diacrylate, triethylene glycol diacrylate, 1,3-butanediol diacrylate, tetramethylene glycol diacrylate, propylene glycol diacrylate, trimethylolpropane triacrylate, trimethylolethane triacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, sorbitol triacrylate, sorbitol tetraacrylate, sorbitol pentaacrylate, sorbitol hexaacrylate, polyester acrylate oligomer, etc.; methacrylic acid esters such as tetramethylene glycol dimethacrylate, triethylene glycol dimethacrylate, trimethylolpropane trimethacrylate, trimethylolethane trimethacrylate, ethylene glycol dimethacrylate, 1,3-butanediol dimethacrylate, pentaerythritol dimethacrylate, pentaerythritol trimethacrylate, dipentaerythritol dimethacrylate, sorbitol trimethacrylate, sorbitol tetramethacrylate, bis-[p-(3-methacryloxy-2-hydroxypropoxy)phenyl]dimethylmethane, bis-[p-(acryloxyethoxy)phenyl]dimethylmethane, etc.; itaconic acid esters such as ethylene glycol diitaconate, propylene glycol diitaconate, 1,3-butanediol diitaconate, 1,4-butanediol diitaconate, tetramethylene glycol diitaconate, pentaerythritol diitaconate, sorbitol tetraitaconate, etc.; crotonic acid esters such as ethylene glycol dicrotonate, tetramethylene glycol dicrotonate, pentaerythritol dicrotonate, sorbitol tetracrotonate, etc.; isocrotonic acids esters such as ethylene glycol diisocrotonate, pentaerythritol diisocrotonate, sorbitol tetraisocrotonate, etc.; maleic acid esters such as ethylene glycol dimaleate, triethylene glycol dimaleate, pentaerythritol dimaleate, sorbitol tetramaleate, etc.

The foregoing esters may be used as mixtures.

Specific examples of the amides of unsaturated carboxylic acids and aliphatic polyvalent amine compounds include methylene bis-acrylamide, methylene bis-methacrylamide, 1,6-hexamethylene bis-methacrylamide, 1,6-hexamethylene bis-acrylamide, diethylenetriamine trisacrylamide, xylylene bis-acrylamide, xylylene bis-methacrylamide, etc.

Other examples of useful polymerizable compounds having an ethylenically unsaturated bond include vinylurethane compounds each having at least two polymerizable vinyl groups in one molecule prepared by the addition reaction of a vinyl monomer having a hydroxy group represented by the general formula (V) described below to a polyisocyanate compound having at least two isocyanate groups in one molecule as described in Japanese Patent Publication No. 41708/73.

$$CH_2=C(R)COOCH_2CH(R')OH \qquad (V)$$

wherein R and R' each represents H or $CH_3$.

When the free radical generating agents according to the present invention are used as photopolymerization initiators for photopolymerizable compositions the photopolymerizable compositions may contain a binder, if desired.

The binder used in the photopolymerizable composition of the present invention must be compatible with the polymerizable ethylenically unsaturated compound and the photopolymerization initiator in order to prevent separation of the binder from the polymerizable ethylenically unsaturated compound and/or the photopolymerization initiator during production of the light-sensitive material. The binder must prevent the separation from the time of preparation of the coating liquid compositions to coating and drying the coated layer or layers. The layer containing the binder must be developed after image exposure as a light-sensitive layer or a resist layer by a solution development or a peel off development. Further, the binder must form a tough layer as a light-sensitive layer or a resist layer. Usually, the binder is properly selected from linear organic polymers.

Specific examples of the binder used in the present invention include chlorinated polyethylene, chlorinated polypropylene, polyacrylic acid alkyl esters (examples of the alkyl group are a methyl group, an ethyl group, a n-butyl group, an iso-butyl group, a n-hexyl group, a 2-ethylhexyl group, etc.), copolymers of an acryl acid alkyl ester (the alkyl group is same as above) and at least one of monomers such as acrylonitrile, vinyl chloride, vinylidene chloride, styrene, butadiene, etc., polyvinyl chloride, a copolymer of vinyl chloride and acrylonitrile, polyvinylidene chloride, a copolymer of vinylidene chloride and acrylonitrile, polyvinyl acetate, polyvinyl alcohol, polyacrylonitrile, a copolymer of acrylonitrile and styrene, a copolymer of acrylonitrile, butadiene, and styrene, polymethacrylic acid alkyl esters (examples of the alkyl group are a methyl group, an ethyl group, a n-propyl group, a n-butyl group, an iso-butyl group, a n-hexyl group, a cyclohexyl group, a 2-ethylhexyl group, etc.), a copolymer of a methacrylic acid alkyl ester (the alkyl is same as above) and at least one monomer such as acrylonitrile, vinyl chloride, vinylidene chloride, styrene, butadiene, etc., polystyrene, poly-α-methylstyrene, polyamides (e.g., 6-nylon, 6,6-nylon, etc.), methyl cellulose, ethyl cellulose, acetyl cellulose, polyvinyl formal, polyvinyl butyral, etc.

Furthermore, when an organic high-molecular weight polymer soluble in water or an alkaline aqueous solution is used, the development can be performed using water or an alkaline aqueous solution. Examples of such high-molecular weight polymers include addition polymers having a carboxylic acid at the side chain, such as methacrylic acid copolymers (e.g., a copolymer of methyl methacrylate and methacrylic acid, a copolymer of ethyl methacrylate and methacrylic acid, a copolymer of butyl methacrylate and methacrylic acid, a copolymer of ethyl acrylate and methacrylic acid, a copolymer of methacrylic acid, styrene, and methacrylic acid, etc.), acrylic acid copolymers (e.g., copolymer of ethyl acrylate and acrylic acid, a copolymer of butyl acrylate and acrylic acid, a copolymer of ethyl acrylate, styrene, and acrylic acid, etc.), an itaconic acid copolymer, a crotonic acid copolymer, and a partially esterified maleic acid copolymer. Other examples of the foregoing high-molecular polymers are acid cellulose derivatives having a carboxylic acid on their side chain.

These high molecular weight polymers may be used alone or in various combinations of two or more kinds of high molecular weight polymers having compatibility with each other with a suitable mixing ratio. Such combinations are possible to the extent that they do not cause any separation during the production steps of the light-sensitive material from the time of preparation of the coating solution to coating and drying.

The molecular weight of the high molecular weight polymer used in the present invention as the binder can be selected over a wide range depending on the type of polymer but is generally from 5,000 to 2,000,000, preferably from 10,000 to 1,000,000.

The photopolymerizable composition of the present invention may further contain a sensitizer. The sensitizer is selected such that it can increase the photopolymerization rate when it is used together with the photopolymerization initiator represented by the general formula (I).

Specific examples of the sensitizer include benzoin, benzoin methyl ether, benzoin ethyl ether, 9-fluorenone, 2-chloro-9-fluorenone, 2-methyl-9-fluorenone, 9-anthrone, 2-bromo-9-anthrone, 2-ethyl-9-anthrone, 9,10-anthraquinone, 2-ethyl-9,10-anthraquinone, 2-t-butyl-9,10-anthraquinone, 2,6-dichloro-9,10-anthraquinone, xanthone, 2-methylxanthone, 2-methoxyxanthone, thioxanthone, benzil, dibenzalacetone, p-(dimethylamino)phenylstyryl ketone, p-(dimethylamino)phenyl p-methylstyryl ketone, benzophenone, p-(dimethylamino)benzophenone (or Michler's ketone), p-(diethylamino)benzophenone, benzanthrone, etc. Among these sensitizers, Michler's ketone is particularly preferred.

It is preferred to incorporate a thermal polymerization preventing agent in the photopolymerizable composition of the present invention for preventing the occurrence of unnecessary thermal polymerization of the polymerizable compound having an ethylenically unsaturated bond in the composition during the production or preservation of the composition. Suitable examples of the thermal polymerization preventing agent used in the present invention include hydroquinone, p-methoxyphenol, di-t-butyl-p-cresol, pyrogallol, t-butylcatechol, benzoquinone, cuprous chloride, phenothiazine, chloranil, naphtylamine, β-naphthol, nitrobenzene, dinitrobenzene, etc.

As the case may be, the photopolymerizable composition of the present invention may further contain dyes or pigments such as Methylene Blue, Crystal Violet, Rhodamine B, Fuchsine, Auramine, azo-dyes, anthraquinone dyes, titanium oxide, carbon black, iron oxide, phthalocyanine pigments, azo-pigments, etc., for the purpose of coloring.

Moreover, the photopolymerizable composition of the present invention may further contain, if necessary, plasticizers. Examples of the plasticizers used in the present invention include phthalic acid esters such as dimethyl phthalate, diethyl phthalate, dibutyl phthalate, dihexyl phthalate, dicyclohexyl phthalate, ditridecyl phthalate, etc.; glycol esters such as dimethyl glycol phthalate, ethylphthalylethyl glycolate, butylphthalylbutyl glycolate, etc.; phosphoric acid esters such as tricresyl phosphate, triphenyl phosphate, etc.; and aliphatic dibasic acid esters such as diisobutyl adipate, dioctyl adipate, dibutyl sebacate, dibutyl maleate, etc.

The photopolymerizable composition of the present invention is coated on a suitable support by a known coating method as a coating liquid prepared by dissolving the above-described components using a solvent. The preferred ratio of each component constituting the photopolymerizable composition of the present invention in the case of preparing the coating liquid is shown in the following table by weight part to 100 parts by weight of the polymerizable compound having an ethylenically unsaturated bond.

|  | Preferred range (parts by weight) | Particularly preferred range (parts by weight) |
| --- | --- | --- |
| Photopolymerization initiator represented by the general formula (I) | 0.01 to 50 | 0.1 to 10 |
| Binder | 0 to 1,000 | 0 to 500 |
| Sensitizer | 0 to 100 | 0 to 20 |
| Thermal polymerization preventing agent | 0 to 10 | 0 to 5 |
| Dye or pigment | 0 to 50 | 0 to 20 |
| Plasticizer | 0 to 200 | 0 to 50 |

The free radical generating agent according to the present invention is particularly useful in photosensitive resist forming compositions which form visible images upon exposure to light without development and used for producing lithographic printing plates, IC circuits or photomasks. In such photosensitive resist compositions, since visible images are obtained directly by only exposing the resist to light, it becomes possible under a yellow safety lamp to check whether the plates are exposed or not, for example, when operation is interrupted in the step of exposing many printing plates at the same time.

Similarly, in the situation in which one large plate is exposed to light many times such as in so-called photo composing step and repeat printing down process for making lithographic printing plates, workers can ascertain immediately what part has been exposed.

The photosensitive resist forming compositions which form visible images immediately upon exposure to light, in which the free radical generating agent according to the present invention can be used advantageously, are generally composed of a photosensitive resist forming compound, a free radical generating agent and a color changing agent as essential components and, if necessary, one or more of plasticizers, binders, dyes which are not color changing agents, pigments, anti-fogging agents and sensitizers for the photosensitive resist forming compound, etc.

The photosensitive resist forming compound can be a compound the physical properties of which (such as solubility, tackiness or adhesive property to base plates, etc.) change upon exposure to light. Examples of these compounds include photosensitive diazo compounds, photosensitive azide compounds, compounds having an ethylenically unsaturated bond and compounds which catalytically react with the acids formed upon exposure to light.

As preferred photosensitive diazo compounds, there are compounds having two or more diazo groups in one molecule, such as the condensation products of a salt of p-diazodiphenylamine with formaldehyde. For example, the diazo compounds include the condensation product of formaldehyde with the phenol salt, the fluorocaprate salt and sulfonates thereof such as the triisopropylnaphthalene sulfonate saltt, the 4,4'-biphenyl-disulfonate salt, the 5-nitro-o-toluenesulfonate salt, the 5-sulfosalicylate salt, the 2,5-dimethylbenzenesulfonate salt, the 2-nitrobenzenesulfonate salt, the 3-chlorobenzenesulfonate salt, the 3-bromobenzenesulfonate salt, the 2-chloro-5-nitrobenzenesulfonate salt, the 2-fluorocaprylnaphthalenesulfonate salt, the 1-naphthol-5-sulfonate salt, the 2-methoxy-4-hydroxy-5-benzoylbenzenesulfonate salt or the p-toluenesulfonate salt, etc. As other preferred diazo compounds, there are the condensation products of 2,5-dimethoxy-4-p-tolylmercaptobenzene diazonium salts with formaldehyde and the condensation products of 2,5-dimethoxy-4-morpholinobenzene diazonium salts with formaldehyde or acetaldehyde, etc.

Further, other examples of useful diazo compounds include the compounds described in U.S. Pat. No. 2,649,373.

The diazo compounds become insoluble upon exposure to actinic radiation, as the diazo groups decompose.

On the other hand, it is possible to use photosensitive diazo compounds which become alkali soluble upon application of actinic radiation. They are compounds having at least one o-quinonediazide group in the molecule, and sulfonic acid ester or sulfonic acid amides of o-quinonediazides are particularly preferred. A number of such compounds are already known. For example, there are the compounds as described in U.S. Pat. Nos. 3,046,110, 3,046,111, 3,046,115, 3,046,119, 3,046,120, 3,046,121, 3,046,122, 3,130,047, 3,130,048, 3,188,210, 3,184,310, 3,102,809, 3,148,983, 3,454,400 and 3,859,099, etc.

Suitable photosensitive azide compounds are aromatic azide compounds wherein the azide group is bonded to the aromatic ring directly or through a carbonyl group or a sulfonyl group. Upon exposure to light as the azide group decomposes to yield a nitrene which causes various reactions and thereby become insoluble. As preferred aromatic azide compounds, there are compounds containing one or more groups such as azidophenyl groups, azidostyryl groups, azidobenzal groups, azidobenzoyl groups or azidocinnamoyl groups. Specific examples of preferred aromatic azide compounds include 4,4'-diazidochalcone, 4-azido-4'-(4-azidobenzoylethoxy)chalcone, N,N-bis-p-azidobenzal-p-phenylenediamine, 1,2,6-tri(4'-azidobezoxy)hexane, 2-azido-3-chlorobenzoquinone, 2,4-diazido-4'-ethoxyazobenzene, 2,6-di(4'-azidobenzal)-4-methylcyclohexanone, 4,4'-diazidobenzophenone, 2,5-diazido-3,6-dichlorobenzoquinone, 2,5-bis(4-azidostyryl)-1,3,4-oxadiazole, 2-(4-azidocinnamoyl)-thiophene, 2,5-di(4'-azidobenzal)cyclohexanone, 4,4'-diazidodiphenylmethane, 1-(4-azidophenyl)-5-furyl-2-penta-2,4-diene-1-one, 1-(4-azidophenyl)-5-(4-methoxyphenyl)-penta-1,4-diene-3-one, 1-(4-azidophenyl)-3-(1-naphthyl)-propene-1-one, 1-(4-azidophenyl)-3-(4-dimethylaminophenyl)-propane-1-one, 1-(4-azidophenyl)-5-phenyl-1,4-pentadiene-3-one, 1-(4-azidophenyl)-3-(4-nitrophenyl)-2-propene-1-one, 1-(4-azidophenyl)-3-(2-furyl)-2-propene-1-one, 1,2,6-tri-(4'-azidobenzoxy)hexane, 2,6-bis(4-azidobenzylidine-p-t-butyl)cyclohexanone, 4,4'-diazidodibenzalacetone, 4,4'-diazidostilbene-2,2'-disulfonic acid, 4'-azidobenzalacetophenone-2-sulfonic acid, 4,4'-diazidostilbene-α-carboxylic acid, di(4-azido-2'-hydroxybenzal)acetone-2-sulfonic acid, 4-azidobenzalacetophenone-2-sulfonic acid, 2-azido-1,4-dibenzenesulfonylaminonaphthalene and 4,4'-diazido-stilbene-2,2'-disulfonic acid anilide, etc.

In addition to these low molecular weight aromatic azide compounds, azide containing polymers as described in Japanese Patent Publication Nos. 9047/69, 31837/69, 9613/70, 24915/70 and 25713/70 are preferred to use.

Suitable compounds having ethylenically unsaturated bonds capable of cross-linking by a photodimerization reaction of the ethylene bond and polymerizable compounds which form insoluble polymers by photopolymerization in the presence of photopolymerization initiators.

As the polymers having ethylenically unsaturated bonds which become insoluble upon photo-dimerization, there are polyesters, polyamides and polycarbonates having a

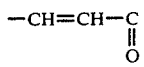

group. Examples of such polymers include photosensitive polymers containing photosensitive groups in the polymer main chain as described in U.S. Pat. Nos. 3,030,208 and 3,707,373, for example, photosensitive polyesters composed of p-phenylene diacrylic acid and diols; photosensitive polymers as described in U.S. Pat. Nos. 2,956,878 and 3,173,787, for example, photosensitive polyesters derived from 2-properidene malonic acid compounds such as cinnamylidene malonic acid, etc., and difunctional glycols; and photosensitive polymers as described in U.S. Pat. Nos. 2,690,966, 2,752,372 and 2,732,301, for example, cinnamic acid esters of hydroxyl group containing polymers such as polyvinyl alcohol, starch, cellulose and the like.

As the polymerizable compounds, there are compounds as described above.

As the color changing agents used for production of the photosensitive resist forming compositions capable of obtaining visible images directly by exposure to light alone, there are two types of compounds: Namely, one is colorless compound which changes to a colored state and the other has an inherent color which discolors or fades by the above-described action by the action of light decomposition product of the free radical generating agent.

As typical color changing agents of the former type, there are arylamines. As the arylamines suitable for such a purpose, there are not only mere arylamines such as primary and secondary aromatic amines but also the so-called leuco dyes, examples of which include the following compounds.

Diphenylamine, dibenzylaniline, triphenylamine, diethylaniline, diphenyl-p-phenylenediamine, p-toluidine, 4,4'-biphenyldiamine, o-chloroaniline, o-bromoaniline, 4-chloro-o-phenylenediamine, o-bromo-N,N-dimethylaniline, 1,2,3-triphenylguanidine, naphthylamine, diaminodiphenylmethane, aniline, 2,5-dichloroaniline, N-methyldiphenylamine, o-toluidine, p,p'-tetramethyldiaminodiphenyl methane, N,N-dimethyl-p-phenylenediamine, 1,2-dianilinoethylene, p,p',p"-hexamethyltriaminotriphenyl methane, p,p'-tetramethyldiaminotriphenyl methane, p,p'-tetramethyldiaminodiphenyl methylimine, p,p',p"-triamino-o-methyltriphenylmethane, p,p',p"-triaminotriphenyl carbinol, p,p'-tetramethylaminodiphenyl-4-anilinonaphthyl methane, p,p',p"-triaminotriphenyl methane and p,p',p"-hexapropyltriaminotriphenyl methane.

As the color changing agents having an inherent color which discolors or fades by the light decomposition product of the free radical generating agent, various dyes such as diphenylmethane type, triphenylmethane type, thiazine type, oxazine type, xanthene type, anthraquinone type, iminonaphthoquinone type and azomethine type dyes are effectively used. Examples of such dyes include the following materials. Brilliant Green, Eosine, Ethyl Violet, Erythrocin B, Methyl Green, Crystal Violet, basic Fuchsine, phenolphthalein, 1,3-diphenyltriazine, Alizarin Red S, Thymolphthalein, Methyl Violet 2B, Quinaldine Red, Rose Bengale, Metanil Yellow, Thymolsulfophthalein, Xylenol Blue, Metyl Orange, Orange IV, diphenylthiocarbazone, 2,7-dichlorofluorescein, Paramethyl Red, Congo Red, Benzopuripurin 4B, α-Naphthyl Red, Nile Blue 2B, Nile Blue A, Phenacetalin, Methyl Violet, Malachite Green, Parafuchsine, Oil Blue #603 (produced by Orient Kagaku Kogyo Co.), Oil Pink #312 (produced by Orient Kagaku Kogyo Co.), Oil Red 5B (produced by Orient Kagaku Kogyo Co.), Oil Scarlet #308 (produced by Orient Kagaku Kogyo Co.), Oil Red OG (produced by Orient Kagaku Kogyo Co.), Oil Red RR (produced by Orient Kagaku Kogyo Co.), Oil Green #502 (produced by Orient Kagaku Kogyo Co.), Spiron Red BEH special (produced by Hodogaya Chemical Co.), m-Cresol purple, Cresol Red, Rhodamine B, Rhodamine 6G, Fast Acid Violet R, Sulfo Rhodamine B, Auramine, 4-p-diethylaminophenyliminoaphthoquinone, 2-carboxyanilino 4-p-diethylaminophenyliminoaphthoquinone, 2-carbostearylamino-4-p-dihydroxyethylaminophenylimino naphthoquinone, p-methoxybenzoyl-p'-diethylamino-o'-methylphenylimino-acetanilide, cyano-p-diethylaminophenyliminoacetanilide, 1-phenyl-3-methyl-4-p-diethylaminophenylimino-5-pyrazolone and 1-β-naphthyl-4-p-diethylaminophenylimino-5-pyrazolone.

In the photosensitive compositions of the present invention, though the light activating agents are stable with the lapse of time, leuco triphenylmethane dyes used as the color changing agents are generally easily oxidized. Therefore, it is effective to incoporate a stabilizer when such dyes are used. As preferred stabilizers for this purpose, there are amines as described in U.S. Pat. No. 3,042,575, zinc oxide, phenols, sulfur compounds as described in U.S. Pat. No. 3,042,516, alkali metal iodides as described in U.S. Pat. No. 3,042,518, organic acids, organic acid anhydrides as described in U.S. Pat. No. 3,082,086, and triaryl compounds of antimony, arsenic, bismuth and phosphorus as described in U.S. Pat. No. 3,377,167.

The photosensitive compositions of the present invention are used by dissolving the above-described components in a solvent and applying to a suitable support by a known method. In the following table, preferred ratios and particularly preferred ratios of each component in a photosensitive composition in accordance with the invention are shown as parts by weight based on 100 parts by weight of the photosensitive resist forming compound.

| | Preferred range (parts by weight) | Particularly preferred range (parts by weight) |
|---|---|---|
| Free radical generating agent of the present invention | 0.01 to 100 | 0.1 to 50 |
| Color changing agent | 0.1 to 50 | 1 to 10 |

| | Preferred range (parts by weight) | Particularly preferred range (parts by weight) |
|---|---|---|
| Plasticizer | 0 to 1,000 | 0 to 500 |
| Binder | 0 to 5,000 | 0 to 1,000 |
| Dye or pigment other than the color changing agent | 0 to 100 | 0 to 50 |
| Anti-fogging agent | 0 to 50 | 0 to 20 |
| Sensitizer for photo-sensitive resist forming compound | 0 to 50 | 0 to 20 |

As the solvent used for applying the photosensitive compositions of the present invention to a support, there may be used ethylene dichloride, cyclohexanone, methyl ethyl ketone, methyl cellosolve acetate, monochlorobenzene, toluene and ethyl acetate, etc.

These solvents are used alone or in admixture. In cases of producing light-sensitive lithographic printing plates, a preferred amount of photosensitive composition is generally in a range of 0.1 to 10.0 g/m² as the solid content and, particularly preferably, 0.5 to 5.0 g/m².

The photosensitive compositions of the present invention are suitable as the light-sensitive layer of light-sensitive lithographic printing plates. As supports suitable for the light-sensitive lithographic printing plates, there are aluminium plates processed to give them a hydrophilic property, for example, aluminium plates treated with a silicate solution, anodized aluminium plates, grained aluminium plates or silica electrodeposited aluminium plates, zinc plates, stainless steel plates, chromium treated copper plates, plastic films processed so as to have a hydrophilic property and paper.

In the case of using photosensitive compositions of the present invention for producing correction plates for printing, films for overhead projectors or films for intermediate originals, suitable supports include transparent films such as polyethylene terephthalate films or cellulose triacetate films, etc., and those plastic films the surface of which has been chemically or physically matted.

When using the photosensitive compositions of the present invention for producing films for photomasks, the preferred supports include polyethylene terephthalate films on which aluminium, aluminium alloy or chromium has been deposited by evaporation and polyethylene terephthalate films having a colored layer.

Further, in cases of using the photosensitive compositions of the present invention as a photosensitive resist forming composition, copper plates, copper plated plates, stainless steel plates and glass plates, etc., can be used as the support.

It is a surprising fact that the free radical generating agents according to the present invention decompose in the photosensitive resist forming composition containing various photosensitive resist forming compounds to efficiently and immediately change the color of a coexistent color changing agent when subjected to the action of light. Consequently, distinct boundaries are obtained between the exposed portions and unexposed portions, which can be observed as visible images having good contrast.

Further, since the free radical generating agents according to the present invention do not hinder the photo decomposition of the photosensitive resist forming compounds, they do not reduce the photosensitivity (resist sensitivity) of the photosensitive resist forming compositions. Moreover, since the free radical generating agents according to the present invention are effective in small amounts, they do not cause deterioration of physical properties of resist images obtained on the photosensitive resist forming composition by image exposure and development thereof. For example, when the photosensitive resist forming composition of the present invention is used as a light-sensitive layer of a light-sensitive lithographic printing plate, properties of the resultant printing plate, such as developability, oil sensitivity, printing stains or printing press life. etc., are the same as those when the free radical generating agent is not added.

Moreover, the free radical generating agent according to the present invention is a good hydrogen abstracting agent and can form an acid when a hydrogen donor is present. Therefore, the free radical generating agent can provide a photodecomposable photosensitive composition by coexisting with a compound which is decomposed in the presence of an acid. Examples of the compounds which are decomposed in the presence of an acid are described in U.S. Pat. Nos. 4,101,323, 4,247,611, 4,248,957, 4,250,247 and 4,311,782, etc.

A synthesis example for the free radical generating agent used in the present invention and examples of the present invention are set forth below, but the present invention should not be construed as being limited thereto.

Unless otherwise specified, all ratios, percents, etc., are by weight.

SYNTHESIS EXAMPLE

Synthesis of 2-Trichloromethyl-5-(p-styryl-styryl)-1,3,4-oxadiazole [Compound No. 1]

31.8 g of terephtharaldehyde was dissolved in 200 ml of methanol and to the solution was added a solution containing 4.3 g of sodium methoxide dissolved in 60 ml of methanol at room temperature. To the reaction solution was added dropwise a solution containing 30.7 g of benzyl triphenyl phosphonium chloride dissolved in 150 ml of methanol at room temperatures and the resulting solution was allowed to react for 2 hours at room temperature. The reaction solution was poured into an excess amount of water and the precipitate thus-formed was collected by filtration and recrystallized from a solvent mixture of ethanol and water to obtain 9.4 g of stilbene-4-aldehyde.

A mixture of 9.4 g of stilbene-4-aldehyde thus-obtained, 10.6 g of malonic acid, 30 ml of pyridine and 3 ml of piperidine was reacted on a steam bath at 100° C. for 4 hours. After the completion of the reaction, the mixture was poured into an exess amount of water and the precipitate thus-obtained was collected and recrystallized from acetic acid to obtain 11.0 g of p-styryl cinnamic acid.

11.0 g of p-styrylcinnamic acid thus-obtained and 6.6 g of p-nitrophenol were refluxed by heating for 1 hour in 50 ml of thionylchloride and 50 ml of benzene. After the excess of thionylchloride and benzene were distilled off, the resulting solid was washed with water and dried. Thus, a stoichiometric amount of p-styrylcinnamic acid p'-nitrophenol ester was obtained.

14.8 g of p-styrylcinnamic acid p'-nitrophenyl ester thus-obtained was added to a solution of 7.6 g of 80% hydrazine hydrate in 75 ml of methanol, and the solution was refluxed for 30 minutes with heating. After cooling the reaction solution by allowing it to stand, the reaction solution was poured into 200 ml of water containing 2 g of sodium hydroxide dissolved therein. Thus, 10.3 g of p-styrylcinnamic acid hydrazide was obtained as crystals.

15.6 g of p-styrylcinnamic acid hydrazide thus-obtained was added to a solution of 17.5 g of hexachloroacetone in 80 ml of acetonitrile, and the solution was refluxed for 30 minutes with heating. The reaction solution was cooled and the precipitate thus-formed was collected by filtration to obtain 22.7 g of N-p-styrylcinnamoyl-N'-trichloroacetyl hydrazide.

22.7 g of N-p-styrylcinnamoyl-N'-trichloroacetyl hydrazide thus-obtained and 150 ml of phosphorus oxychloride were refluxed for 2 hours with heating. The mixture was added to 1000 g of ice water. The resulting precipitate was recrystallized from a solvent mixture of ethyl acetate and ethanol to obtain 15.2 g of 2-trichloromethyl-5-(p-styryl-styryl)-1,3,4-oxadiazole (melting point: 176.5° to 178.5° C.

EXAMPLE 1

On an aluminum plate, the surface of which had been grained by means of a nylon brush and then subjected to silicate treatment, was coated the light-sensitive solution having the compositions described below using a rotary coating machine and dried at 100° C. for 3 minutes to prepare a light-sensitive layer of a light-sensitive plate.

| Light-Sensitive Solution: | |
|---|---|
| Copolymer of methyl methacrylate and methacrylic acid (molar ratio of copolymerization: 85:15; intrinsic viscosity in methyl ethyl ketone at 30° C.: 0.166) | 62 g |
| Trimethylolpropane triacrylate | 38 g |
| Compound represented by the general formula (I) | 2 g |
| Triphenyl phosphate | 10 g |
| Ethyl cellosolve | 650 ml |
| Methylene chloride | 350 ml |

A step wedge (density step difference of 0.15 and density step number of 15 steps) was placed on the light-sensitive plate, the plate was exposed to a metal halide lamp (0.5 kW) using a vacuum printing device, and after the light exposure, the light-sensitive plate was developed using a developing solution having the following composition.

| Developing Solution: | |
|---|---|
| Trisodium phosphate | 25 g |
| Monosodium phosphate | 5 g |
| Buthyl cellosolve | 70 g |
| Surface active agent | 2 ml |
| Water | 1 l |

The highest step number corresponding to the step wedge of the developed image is used to indicate the sensitivity of the light-sensitive plate and is shown in Table 1 below. A greater step number means a higher sensitivity. Also, the sensitivity of the plate which does not contain the free radical generating agent represented by the general formula (I) is shown as Comparative Sample (1) in Table 1.

TABLE 1

| | Sensitivity of Compound Represented by the General Formula (I) | |
|---|---|---|
| Sample No. | Compound represented by the general formula (I) | Highest step number of step wedge |
| 1 [Invention] | No. 1 | 14 |
| 2 [Invention] | No. 8 | 14 |
| 3 [Invention] | No. 11 | 13 |
| 4 [Invention] | No. 15 | 13 |
| Comparative Sample (1) | None | 0 |

As is apparent from the results shown in Table 1, the light-sensitive plates using the free radical generating agent represented by the general formula (I) as a photopolymerization initiator have extremely high sensitivity and thus the desired effects of the present invention are sufficiently recognized.

EXAMPLE 2

On the aluminum plate used in Example 1 was coated the light-sensitive solution having the composition described below to prepare a light-sensitive printing plate.

| Light-Sensitive Solution: | |
|---|---|
| Pentaerythritol tetraacrylate | 40 g |
| Compound represented by the general formula (I): Compound No. 9 | 2 g |
| Copolymer of benzyl methacrylate/ methacrylic acid (73/27 in mole ratio) | 60 g |
| Methyl ethyl ketone | 400 ml |
| Methylcellosolve acetate | 300 ml |

The light-sensitive printing plate thus-prepared was imagewise exposed to light using a jet printer (having a super high pressure mercury lamp of 2 kW, manufactured by ORC Seisakusho) and developed with a developing solution having the following composition, whereby the unexposed portions are removed to obtain the clear image.

| Developing Solution: | |
|---|---|
| Anhydrous sodium carbonate | 10 g |
| Butyl cellusolve | 5 g |
| Water | 1 l |

Further, the unexposed light-sensitive printing plate was subjected to a forced durability test (at 45° C. and 75% RH for 5 days) and then exposed to light and developed. The same clear image was obtained as that formed in the printing plate just after the preparation.

EXAMPLE 3

On the aluminum plate used in Example 1 was coated the light-sensitive solution having the compositions described below to prepare a light-sensitive printing plate.

| Light-Sensitive Solution: | |
|---|---|
| Trimethylolpropane trimethacrylate | 0.30 g |
| Triethyleneglycol diacrylate | 0.08 g |
| Copolymer of methyl methacrylate, ethyl acrylate and methacrylic acid (80/10/10 in mole ratio) | 0.62 g |
| Compound represented by the general formula (I): Compound No. 11 | 0.02 g |

-continued

| Light-Sensitive Solution: | |
|---|---|
| Leuco crystal violet | 0.008 g |
| Methyl ethyl ketone | 10 g |

When this light-sensitive lithographic printing plate was subjected to imagewise exposure, print-out images having high contrast were obtained.

Then, a lithographic printing plate was obtained by removing the unexposed portions using a developing solution composed of 1.2 g of sodium hydroxide, 300 ml of isopropyl alcohol and 900 ml of water.

EXAMPLE 4

On an aluminum plate having a thickness of 0.15 mm, the surface of which had been grained, the light-sensitive solution described below was coated by a whirler and dried at 100° C. for 2 minutes to prepare a light-sensitive lithographic printing plate.

| Light-Sensitive Solution: | |
|---|---|
| Esterified product of naphthoquinone-(1,2)diazido(2)-5-sulfonylchloride and pyrogallol acetone resin | 0.75 g |
| Cresol novolak resin | 2.1 g |
| Tetrahydrophthalic acid anhydride | 0.15 g |
| Crystal violet | 0.02 g |
| Free radical generating agent (as shown in Table 2 below) | 0.03 g |
| Ethylene dichloride | 18 g |
| Methyl cellosolve | 12 g |

The coating amount after drying was 2.2 g/m².

After the light-sensitive lithographic printing plates were exposed to light at a distance of 70 cm by a carbon arc lamp of 30 amperes, they were developed at 25° C. for 60 seconds using a developing solution prepared by diluting DP-1 (trade name, a developing solution for positive type PS plate manufactured by Fuji Photo Film Co., Ltd.) to 6 times in volume with water, and the sensitivity was measured.

In this case, the optimum exposure time was taken as the time at which 5 steps of a gray scale having an optical density difference of 0.15 became completely clear.

Optical densities of the exposed portion and the unepoxed portion on the light-sensitive layer after subjection to a forced durability test were measured using a Macbeth reflection densitometer.

Further, the above-described measurement was repeated after the light-sensitive lithographic printing plates were subjected to a forced durability test. The forced durability test was carried out at 45° C. in the temperature, 75% humidity, for 7 days.

The images obtained upon exposure to light became clearer as the difference (ΔD) between the density of exposed portion and the unexposed portion increased.

TABLE 2

Properties of Light-sensitive Lithographic Printing Plate

| | | Optimum Exposure Time for Forming Resist Image (resist sensitivity) (seconds) | Optical Density of Light-sensitive Layer | | | | | |
|---|---|---|---|---|---|---|---|---|
| | | | 1 Day after Coating | | | After Forced Durability Test (45° C., 75%, for 7 days) | | |
| Sample No. | Free Radical Generating Agent | | Unexposed Portion | Exposed Portion | ΔD | Unexposed Portion | Exposed Portion | ΔD |
| 1. Comparison | None | 65 | 0.89 | 0.89 | 0.00 | 0.89 | 0.89 | 0.00 |
| 2. Invention | Compound No. 1 | 68 | 0.89 | 0.71 | 0.18 | 0.89 | 0.72 | 0.17 |
| 3. Comparison | 2,4-Bis(trichloromethyl)-6-(p-methoxystyryl)-s-triazine | 75 | 0.87 | 0.71 | 0.16 | 0.86 | 0.72 | 0.14 |
| 4. Comparison | Naphthoquinone-1,2-diazido-(2)-4-sulfonyl chloride | 66 | 0.88 | 0.78 | 0.10 | 0.87 | 0.82 | 0.05 |

As is apparent from the results shown in Table 2, the free radical generating agent No. 1 according to the present invention exhibits excellent stability with time in comparison with the known compound, i.e., naphthoquinone-1,2-diazido-(2)-4-sulfonylchloride. Further, although known 2,4-bis(trichloromethyl)-6-(p-methoxystyryl)-s-triazine has good stability with time similar to the free radical generating agent No. 1 according to the present invention, the known 2,4-bis(trichloromethyl)-6-(p-methoxystyryl)-s-triazine is inferior in print-out property and in that the resist sensitivity is reduced.

EXAMPLE 5

On the aluminum plate used in Example 4 was coated the light-sensitive solution having the composition described below to prepare a light-sensitive printing plate.

| Light-Sensitive Solution: | |
|---|---|
| Esterified product of naphthoquinone-(1,2)-diazido-(2)-5-sulfonyl chloride and cresol novolak resin | 0.75 g |
| Cresol novolak resin | 2.10 g |
| Tetrahydrophthalic acid anhydride | 0.15 g |
| Free radical generating agent represented by the general formula (I): Compound No. 17 | 0.02 g |
| Crystal violet | 0.01 g |
| Oil blue #603 (manufactured by Orient Kagaku Kogyo Co.) | 0.01 g |
| Ethylene dichloride | 18 g |
| Methyl cellosolve acetate | 12 g |

The coating amount after drying was 2.2 g/m².

Clear print-out images could be obtained on this light-sensitive lithographic printing plate by image exposure without development. Since the exposed portions faded and the unexposed portions maintained their original density, details of the images could be discerned under a safety lamp.

EXAMPLE 6

On the aluminum plate used in Example 1 was coated the light-sensitive solution having the composition described below to prepare a light-sensitive printing plate.

| Light-Sensitive Solution: | |
| --- | --- |
| p-Toluenesulfonate of condensation product of p-diazodiphenylamine and paraformaldehyde | 0.2 g |
| Polyvinyl formal | 0.75 g |
| Compound No. 1 (free radical generating agent) | 0.02 g |
| N,N—dimethylaniline | 0.02 g |
| Methyl cellosolve | 20 g |
| Methanol | 5 g |

The coating amount after drying was 1.0 g/m².

When this light-sensitive lithographic printing plate was subjected to imagewise exposure, print-out images the details of which could be discerned under a safety lamp were obtained, because the exposed portions colored violet and the unexposed portions maintained their original yellow color.

EXAMPLE 7

On the aluminum plate used in Example 1 was coated the light-sensitive solution having the composition described below to prepare a light-sensitive printing plate.

| Light-Sensitive Solution: | |
| --- | --- |
| Polyester synthesized by condensation of equimolar amounts of ethyl p-phenylenediacrylate and 1,4-bis(β-hydroxyethoxy)cyclohexane | 0.5 g |
| 2-Benzoylmethylene-3-methyl-β-naphthothiazoline | 0.03 g |
| Compound No. 1 (free radical generating agent) | 0.008 g |
| Leuco crystal violet | 0.008 g |
| Monochlorobenzene | 9 g |
| Ethylene dichloride | 6 g |

The coating amount after drying was 1.2 g/m².

When this light-sensitive lithographic printing plate was subjected to imagewise exposure, print-out images the details of which could be discerned under a safety lamp were obtained, because the exposed portions colored violet and the unexposed portions maintained their original yellow color.

While the invention has been described in detail and with reference to specific embodiments thereof, it will be apparent to one skilled in the art that various changes and modifications can be made therein without departing from the spirit and scope thereof.

What is claimed is:

1. A photosensitive composition comprising in admixture a photosensitive diazo compound or a photopolymerizable compound having an ethylenically unsaturated bond, and a 2-halomethyl-5-substituted-1,3,4-oxadiazole compound represented by general formula (I) and a color changing agent which is colored and discolors or fades by the action of a light decomposition product of the 2-halomethyl-5-substituted-1,3,4-oxadiazole compound:

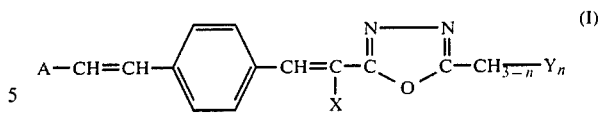

wherein A represents a substituted or unsubstituted aromatic residue; X represents a hydrogen atom, a cyano group, an alkyl group or an aryl group; Y represents a chlorine atom or a bromine atom; and n represents an integer of 1 to 3; and wherein the 2-halomethyl-5-substituted-1,3,4-oxadiazole compound and the color changing agent are present in an amount of from 0.01 to 50 parts by weight and up to 50 parts by weight, respectively, based on 100 parts by weight of the photosensitive diazo compound or the photopolymerizable compound having an ethylenically unsaturated bond.

2. A photosensitive composition as claimed in claim 1, wherein a substituent for the substituted aromatic residue is an alkyl group having from 1 to 2 carbon atom, an alkoxy group having from 1 to 2 carbon atoms, a halogen atom, a nitro group, a phenyl group, a carboxy group or a cyano group.

3. A photosensitive composition as claimed in claim 1, wherein the alkyl group represented by X is an alkyl group having from 1 to 3 carbon atoms.

4. A photosensitive composition as claimed in claim 1, wherein the aryl group represented by X is a monocyclic or bicyclic aryl group.

5. A photopolymerizable composition comprising in admixture:
   (1) a photopolymerizable compound which is an ester of an unsaturated carboxylic acid, and
   (2) a photopolymerization initiator, wherein said photopolymerization initiator is a 2-halomethyl-5-substituted-1,3,4-oxadiazole compound represented by the following general formula (I):

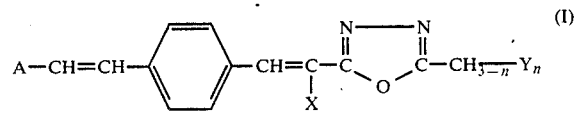

wherein A represents a substituted or unsubstituted aromatic residue; X represents a hydrogen atom, a cyano group, an alkyl group or an aryl group; Y represents a chlorine atom or a bromine atom; and n represents an integer of 1 to 3, and wherein said photopolymerization initiator is present in an amount of from 0.01 to 50 parts by weight based on 100 parts by weight of said photopolymerizable compound.

6. A composition as claimed in claim 5 wherein the aromatic residue represented by A is an aryl group or a heteroaromatic residue.

7. A composition as claimed in claim 5, wherein the aromatic residue is a monocyclic group or a bicyclic group.

8. A composition as claimed in claim 5, wherein the composition contains a binder.

9. A composition as claimed in claim 5, wherein the composition contains a sensitizer.

* * * * *